US009008749B2

(12) United States Patent
Buzug et al.

(10) Patent No.: US 9,008,749 B2
(45) Date of Patent: Apr. 14, 2015

(54) APPARATUS AND METHOD FOR INFLUENCING AND/OR DETECTING MAGNETIC PARTICLES IN A FIELD OF VIEW HAVING AN ARRAY OF SINGLE-SIDED TRANSMIT COIL SETS

(75) Inventors: Thorsten Manuel Buzug, Groβ Sarau (DE); Timo Frederik Sattel, Lübeck (DE); Tobias Knopp, Lübeck (DE); Sven Biederer, Lübeck (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/576,757

(22) PCT Filed: Jan. 28, 2011

(86) PCT No.: PCT/IB2011/050374
§ 371 (c)(1),
(2), (4) Date: Aug. 2, 2012

(87) PCT Pub. No.: WO2011/095916
PCT Pub. Date: Aug. 11, 2011

(65) Prior Publication Data
US 2012/0310076 A1    Dec. 6, 2012

(30) Foreign Application Priority Data
Feb. 8, 2010   (EP) .................................... 10152907

(51) Int. Cl.
*A61B 5/05*    (2006.01)
(52) U.S. Cl.
CPC ................. *A61B 5/05* (2013.01); *A61B 5/0515* (2013.01)
(58) Field of Classification Search
CPC ................................. A61B 5/05; A61B 5/0515
USPC ........................................................ 600/409
See application file for complete search history.

(56) References Cited

U.S. PATENT DOCUMENTS 6,942,148 B2 *  9/2005  Raggam ........................ 235/451
7,309,439 B2 * 12/2007  Fernandez et al. ............ 210/695
(Continued)

FOREIGN PATENT DOCUMENTS

DE          10151778 A1     10/2001
EP          1304542 A2      10/2002
(Continued)

OTHER PUBLICATIONS

Sattel et al: "Fast Track Communication; Single-Sided Device for Magnetic Particle Imaging", Journal of Physics D. Applied Physics, IOP Publishing, Bristol, GB, vol. 42, No. 2, Jan. 21, 2009, pp. 1-5, XP020149056.
Knopp et al.: "Field-Free Line Formation in a Magnetic Field", Journal of Physics A: Mathematical and Theoretical, vol. 43, Jan. 2002, Dec. 8, 2009, XP009147878, pp. 1-9.
(Continued)

*Primary Examiner* — Long V Le
*Assistant Examiner* — Colin T Sakamoto

(57) ABSTRACT

The present invention relates to an apparatus and a method for influencing and/or detecting magnetic particles in a field of view. To increase the field of view and, at the same time, allow access to the patient during imaging, the apparatus comprises two or more transmit coil sets (200) wherein neighboring coil sets are partially overlapping, a transmit coil set comprising: a pair (210) of concentrically arranged selection field coils (211, 212) for generating a magnetic selection field (50) having a pattern in space of its magnetic field strength such that a first sub-zone (52) having a low magnetic field strength and a second sub-zone (54) having a higher magnetic field strength are formed in the field of view (28), and at least one pair (220, 230) of drive field coils (221, 222; 231, 232) for changing the position in space of the two sub-zones (52, 54) in the field of view (28) by means of a magnetic drive field so that the magnetization of the magnetic particles changes locally, said at least one pair (220, 230) of drive field coils being arranged parallel to said pair (210) of selection field coils (211, 212) and being formed by two neighboring coil loops.

14 Claims, 9 Drawing Sheets

(56) References Cited

U.S. PATENT DOCUMENTS

| | | | |
|---|---|---|---|
| 2006/0100509 A1* | 5/2006 | Wright et al. | 600/426 |
| 2009/0096413 A1* | 4/2009 | Partovi et al. | 320/108 |

FOREIGN PATENT DOCUMENTS

| | | | |
|---|---|---|---|
| EP | 1304542 A3 | 10/2002 | |
| WO | 2004091386 A2 | 10/2004 | |
| WO | 2004091390 A2 | 10/2004 | |
| WO | 2004091393 A1 | 10/2004 | |
| WO | 2004091394 A2 | 10/2004 | |
| WO | 2004091394 A3 | 10/2004 | |
| WO | 2004091395 A2 | 10/2004 | |
| WO | 2004091395 A3 | 10/2004 | |
| WO | 2004091721 A1 | 10/2004 | |
| WO | WO2004091386 A2 | 10/2004 | |
| WO | WO2004091390 A2 | 10/2004 | |
| WO | 2006136865 A1 | 12/2006 | |
| WO | WO 2008078257 A2 * | 7/2008 | |
| WO | 2010067248 A1 | 6/2010 | |
| WO | WO 2011010243 A1 * | 1/2011 | |

OTHER PUBLICATIONS

Gleich et al: "Tomographic imaging using the nonlinear reponse of magnetic particles", Nature Publishing Group, vol. 435, Jun. 30, 2005, pp. 1214-1217.

T. Knopp et al., "Field-Free Line Formation in a Magnetic Field", Journal of Physics A: Mathematical and Theoretical; Fast Track Communication; 43 (2010) Jan. 2002, pp. 1-9.

T.F. Sattel et al., "Single-Sided Device for Magnetic Particle Imaging", Journal of Physics D: Applied Physics; Fast Track Communication; 42 No. 2 (Jan. 21, 2009) pp. 1-7.

Knopp et al: "Generation of a Static Magnetic Field-Free Line Using Two Maxwell Coil Pairs", Applied Physics Letters, AIP, American Institute of Physics, Melville, NY, US, vol. 97, No. 9, Aug. 30, 2010, pp. 92505, XP009142504.

Sattel et al: "Single-Sided Coil Configuration for Magnetic Particle Imaging", IFMBE Proceedings (International Federation for Medical and Biological Engineering), Springer, DE, vol. 25/7, Sep. 12, 2009, pp. 281-284, XP009130416.

* cited by examiner

APPARATUS AND METHOD FOR INFLUENCING AND/OR DETECTING MAGNETIC PARTICLES IN A FIELD OF VIEW HAVING AN ARRAY OF SINGLE-SIDED TRANSMIT COIL SETS

FIELD OF THE INVENTION

The present invention relates to an apparatus and a method for influencing and/or detecting magnetic particles in a field of view.

Further, the present invention relates to a computer program for implementing said method on a computer and for controlling such an apparatus as well as to a transmit coil set for use in such an apparatus.

The present relates particularly to the field of magnetic particle imaging (MPI).

BACKGROUND OF THE INVENTION

Magnetic fields play an important role in a wide range of applications. They are used for instance in electric motors, dynamos and for signal transmission of radio or television. Furthermore, magnetic fields are used for medical diagnosis, where the most prominent example is magnetic resonance imaging (MRI). In each of these applications, the magnetic field is tailored to fulfill certain needs. For instance, in MRI, the formation of two field configurations is required: A spatially homogeneous and a linearly increasing gradient field. These special fields can be generated by electromagnetic coils, whereas the coil geometry and the applied current determine the field characteristics. For these simple field configurations, the optimal coil topology is well known. A homogeneous magnetic field is generated by a Helmholtz coil pair consisting of two identical coils that are placed symmetrically along a common axis, and separated by distance R equal to the coil radius. Each coil carries equal current owing in same direction. Similarly, a gradient field is generated by a Maxwell coil pair, which has the same topology but current owing in opposing direction and a larger coil distance of $R\sqrt{3}$.

Magnetic Particle Imaging (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects— e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

Beside the above described conventional coil setup where the object of interest is positioned in the center of the cylindrical scanner, a so-called single-sided coil arrangement has been published in the paper of Sattel T F, Knopp T, Biederer S, Gleich B, Weizenecker J, Borgert J, Buzug T M (2009) "Single-Sided Device for Magnetic Particle Imaging", Journal of Physics D: Applied Physics, 42, 2:5. In such an arrangement, which will also be called single-sided basis coil set, the object is positioned in front of the scanner setup and, thus, its total size does not matter. While the different scanner designs aim at different applications, so far, the major drawback of the 3D single-sided scanner is that it only allows for imaging of a relatively small field of view. Actually, the field is restricted in all three directions by the dimensions of the transmit coils and the sensitivity of the receive coils.

SUMMARY OF THE INVENTION

It is an object of the present invention to provide an apparatus and a method for influencing and/or detecting magnetic particles in a field of view having an increased field of view, preferably in all dimensions, an improved image quality at the boundary of the field of view, and, hence, allowing for imaging of larger areas than then known apparatus and methods, in particular than the known single-sided coil arrangement.

It is a further object of the present invention to provide a computer program for implementing said method on a computer and for controlling such an apparatus as well as a transmit coil set for use in such an apparatus.

In a first aspect of the present invention an apparatus for influencing and/or detecting magnetic particles in a field of view is proposed, which apparatus comprises:

i) two or more transmit coil sets, wherein neighboring coil sets are partially overlapping, a transmit coil set comprising:
 a pair of concentrically arranged selection field coils for generating a magnetic selection field having a pattern in space of its magnetic field strength such that a first sub-zone having a low magnetic field strength and a second sub-zone having a higher magnetic field strength are formed in the field of view, and
 at least one pair of drive field coils for changing the position in space of the two sub-zones in the field of view by means of a magnetic drive field so that the magnetization of the magnetic particles changes locally, said at least one pair of drive field coils being arranged parallel to said pair of selection field coils and being formed by two neighboring coil loops
ii) generator means for generating current signals for provision to said selection field coils and said drive field coils for generating the desired magnetic fields by said coils, and
iii) control means for controlling said generator means to generate direct currents of opposite directions for provision to the two selection field coils of said pair of selection field coils and alternate currents of opposite directions for provision to the two drive field coils of said at least one pair of drive field coils.

In a further aspect of the present invention a corresponding method is presented as well as computer program for implementing said method.

In still a further aspect of the present invention a corresponding transmit coil set is provided for use in such an apparatus.

Preferred embodiments of the invention are defined in the dependent claims. It shall be understood that the claimed method, the claimed transmit coil set and the claimed computer program have similar and/or identical preferred embodiments as the claimed apparatus and as defined in the dependent claims.

The present invention is based on the idea to extend the single-sided coil arrangement comprising a single transmit coil set for MPI as described in the above cited paper of Sattel et al. According to the present invention additional transmit coil sets are complemented that are capable of generating magnetic fields orientated perpendicular to the axial scanner axis z in front of the scanner device. The single FFP, i.e. the first sub-zone having a low magnetic field strength, can then be moved to any position on a multi-dimensional trajectory by applying appropriate currents to the coils of the transmit coil sets.

A further aspect of the present invention is, that the two or more transmit coil sets are overlapping and coupled. In that way, the FFP can be moved seamlessly over an arbitrarily large field of view, which is only limited by the number of overlapping transmit coil sets.

The proposed invention thus provides the following features:
 it produces an enlarged field of view of arbitrary dimension in horizontal direction, e.g. parallel to the patient table;
 it produces higher image quality due to a synergy effect between neighboring transmit coil sets;
 it achieves a larger axial penetration depth;
 the power consumption of a single transmit coil set may be reduced;
 it is capable of multiple field free points processing (mFFP);
 it allows for fast parallel image reconstruction;
 it provides a small SAR (Specific Absorption Rate) also for large fields of view; and
 it allows for large scale catheter interventions.

To generate the desired magnetic fields, appropriate currents are provided to the coils of the transmit coil sets. Said coils are generated by appropriate generator means under control of control means. In particular, looking at one transmit coil set, the magnetic selection field, which is generally a homogeneous magnetic field, is generated by providing direct currents of opposite directions to the two selection field coils of a pair. To generate a magnetic drive field in a desired direction alternate currents of opposite directions are provided to the two drive field coils of the at least one pair of drive field coils of a transmit coil set. Hence, to generate a magnetic drive field perpendicular to the coil axis, contrary to the single-sided coil arrangement described in the above-cited paper of Sattel et al., separate drive field coils are used for generating said magnetic drive fields, i.e. selection field coils are not used for this purpose. Further, such pair of drive field coils is formed by two neighboring coil loops so that the magnetic fields generated by both loops when alternate current of opposite directions are provided to said coil loops, add up, at least in a central region, i.e. where two neighboring branches of said coil loops are directly located next to each other.

In a preferred embodiment two pairs of drive field coils are provided in a transmit coil set (preferably in each transmit coil set), said two pairs of drive field coils being arranged parallel to each other and to said pair of selection field coils and being rotated with respect to each other by a rotation angle in the range between 0° and 180°. This enables the movement of the FFP in two dimension perpendicular to the coil axis. Hence, a slice image can be obtained if the proposed apparatus is used for imaging. If in addition the imaged object is moved through the plane of said slice, a three-dimensional imaging is possible.

Further, in an embodiment said control means is adapted for controlling said generator means to generate alternate currents of opposite directions for provision to the two selection field coils of said pair of selection field coils in addition to the direct currents of opposite directions. In this way the selection field coils are additionally used as drive field coils and enable a movement of the FFP along the coils axis. If the transmit coil sets each comprise two pairs of drive field coils, a movement of the FFP in three dimensions is thus possible, enabling, for instance, a three-dimensional imaging. If the transmit coil sets each comprise only a single pair of drive field coils, a movement of the FFP in two dimensions is possible (in a plane through the coil axis). However, also in this way a three-dimensional imaging is possible if the imaged object is moved through the plane, in which the FFP can be moved.

As mentioned above, the pairs of drive field coils are lying above each other, but are rotated with respect to each other via a rotation angle in the range between 0° and 180°. A preferred rotation angle, however, lies in the range between 75° and 105°. The best efficiency for generating magnetic drive fields is achieved if the rotation angle is (exactly or approximately) 90°.

Generally, the drive field coils of each or all pairs may be formed by various coil loops. However, the obtainable magnetic drive field can be better calculated and predetermined if all drive field coils are formed by identical coil loops, as is preferred in an embodiment of the present invention.

Advantageous layouts of the drive field coils are D-shaped or rectangular-shaped coil loops, wherein two linear branches of said loops are directly neighboring each other. Other layouts of coils, however, can also be used as long as they allow to generate magnetic drive fields in the desired direction and with a desired strength.

According to a further embodiment, the two coil loops of a pair of drive field coils are arranged symmetrical to a symmetry plane going through a coil axis to which said selection field coils are arranged concentric. This provides a symmetric and compact layout of the transmit coil set, in particular if, as proposed according to a further embodiment, the pair of selection field coils and the at least one pair of drive field coils of a transmit coil set have identical outer dimensions and are disk-like arranged above each other. This enables the arrangement of the transmit coil sets, in particular a plurality of mutually overlapping transmit coil sets, to be arranged substantially in a coil plane, for instance, as proposed in a preferred embodiment, in a plane parallel to the surface of a patient table on which a patient can be positioned. For instance, the plurality of transmit coil sets may be integrated into the patient table itself which enables the medical staff to freely access a patient lying on a patient table while simultaneously generating images from a desired area of interest of the patient.

In an advantageous embodiment, the apparatus further comprises iv) receiving means comprising at least one receiving coil for acquiring detection signals, which detection signals depend on the magnetization in the field of view, which magnetization is influenced by the change in the position in space of the first and second sub-zone, and v) processing means for processing said detection signals, in particular for reconstructing an image from said detection signals and/or for localizing said magnetic particles within the field of view, in particular within an object placed within the field of view.

While generally with the apparatus and method according to the present invention magnetic particles can be influenced, for instance can be moved through a patient's body to a desired location, for instance to deposit any drugs there or to move a medical instrument there, another main field of the application is the field of imaging, for which purpose receiving means and processing means are provided according to this preferred embodiment. The at least one receiving coil for acquiring the detection signals may be a separate receiving coil (or a set of receiving coils), but may also be integrated into the transmit coil sets. For instance, each transmit coil set may additionally comprise a single receiving coil. Alternatively, the transmit coils, i.e. the selection field coils and/or the drive field coils, of the transmit coil sets can be used as receiving coils.

To be effective in a larger field of view, the apparatus does not only comprise a low number of transmit coil sets, but preferably a plurality of transmit coil sets, which are equidistantly spaced and substantially arranged within a flat or curved plane. As mentioned above, such a flat plane can be a plane parallel to the surface of a patient table. However, the transmit coil sets may also be arranged in one or more flat or curved planes, for instance partly surrounding the area of interest of a patient, but not completely surrounding the patient as is the case in a conventional MPI apparatus.

According to another preferred embodiment, the control means is adapted for controlling said generator means to generate currents for provision to the coils of the transmit coil sets such that for transfer of the first sub-zone from a first transmit coil set to a second transmit coil set, the first sub-zone is driven to the border of the field of view of the first transmit coil set, the magnetic selection field of the first transmit coil set is decreased and the magnetic selection field of the second transmit coil set is increased. This provides the advantage that the overlapping transmit coil sets are coupled and that the FFP (i.e. the first sub-zone) can be moved seamlessly over an arbitrarily large field of view, which movement is only limited by the number of overlapping transmit coil sets.

If the transmit coil sets were seen as independent units, each transmit coil set would disturb the FFPs of the neighboring transmit coil set. Therefore, in this preferred embodiment a correct "handshaking" is provided. In particular, it is provided that a stable FFP quality is achieved if a transmit coil set drives its FFP to the boundary of its field of view. At the same time, the magnetic gradient field of the neighboring transmit coil set is being increased to receive the FFP, i.e. to take over the FFP to the next transmit coil set. Simultaneously, the first transmit coil set decreases its magnetic gradient field (i.e. its magnetic selection field) to handover the FFP to the neighboring transmit coil set. The simultaneous increasing and decreasing process of the neighboring transmit coil sets are carefully steered to ensure a shift invariant quality of the FFP gradient. A seamless motion of the FFP over the whole array of transmit coil sets can thus be achieved with this embodiment.

As mentioned above, not only a single FFP can be moved over an array of transmit coil sets, but two or more FFPs can be generated and simultaneously moved if, as proposed according to another embodiment, the control means is adapted for controlling the generator means to generate currents for provision to the plurality of transmit coil sets in an appropriate way. Generally, each transmit coil set can generate its own FFP, and it may be possible to simultaneously move all FFPs in the same direction and with the same speed in this way. Such an embodiment of using two or more FFPs simultaneously provides the advantage that data acquisition time can be shortened and/or that a larger field of view can be imaged simultaneously and/or in a shorter time.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition will also be given. The similarities and differences between the two embodiments will be pointed out.

Figure 1:
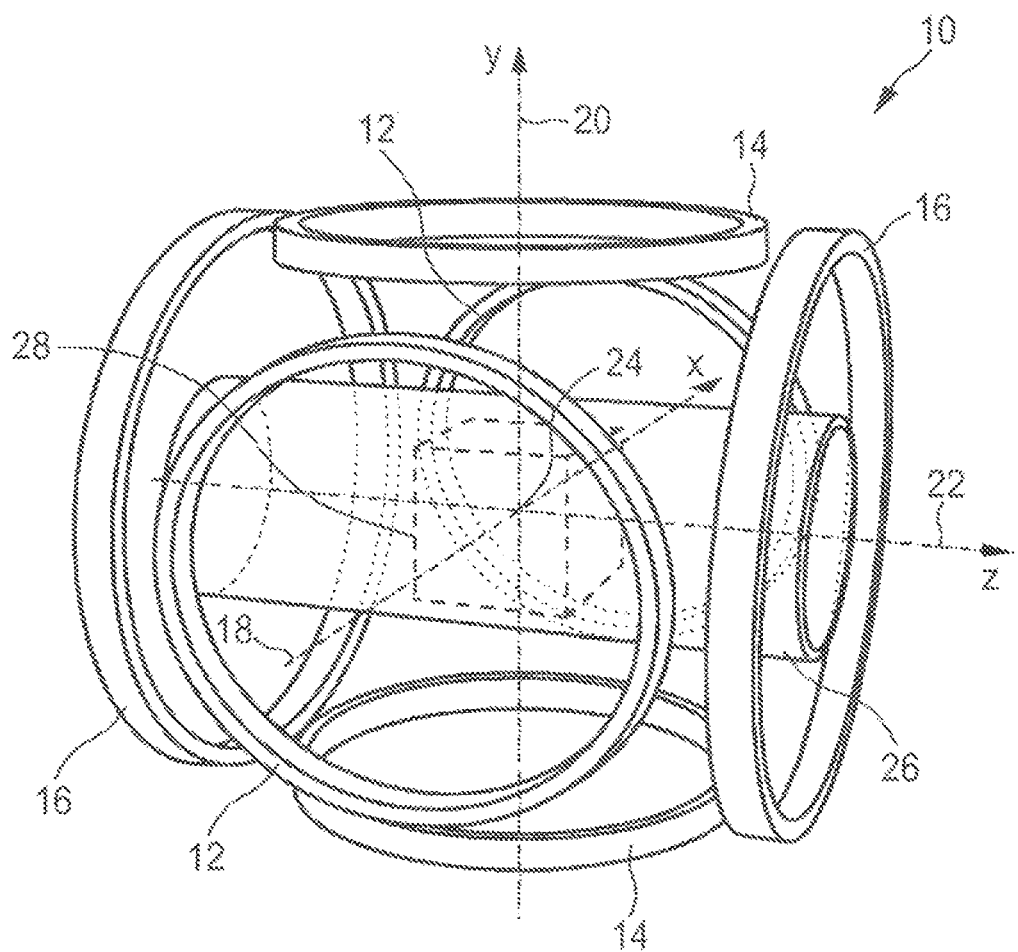
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x- and z-axes are horizontal. The coil pairs 12, 14, 16 are named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils. When more convenient, the coordinate axes and the coils shall be labeled with $x_1$, $x_2$, and $x_3$, rather than x, y, and z.

The scanner 10 can be set to direct a predetermined, time-dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

Figure 2:
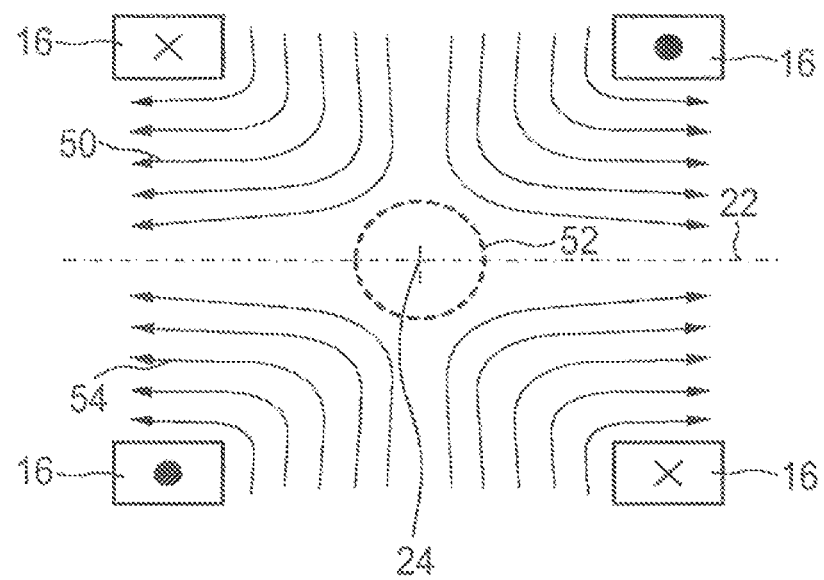
FIG. 2 shows an example of the selection field pattern produced by an apparatus as shown in FIG. 1.

The magnetic selection field, which is generally a magnetic gradient field, is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28, the (overall) magnetization in the field of view 28 changes. By determining the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superposed to the selection field 50.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^\pm$-coil is $I^D_3 + I^F_3 \pm I^S$. The current flowing through the remaining two coil pairs 12, 14 is $I^D_k + I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field-free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time-dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to a patient.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time-dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged is placed in the bore 26 such that the patient's volume of interest—that volume of the patient (or object) that shall be imaged—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the strength of the gradient of the magnetic selection field and on the other hand on the field strength of the magnetic field required for saturation, which in turn depends on the magnetic particles. For a sufficient saturation of typical magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Prior to the diagnostic imaging of, for example, a tumor, the magnetic particles are brought to the volume of interest, e.g. by means of a liquid comprising the magnetic particles which is injected into the body of the patient (object) or otherwise administered, e.g. orally, to the patient.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 µm, a magnetic field of approximately 800 A/m (corresponding approximately to a flux density of 1 mT) is then required, whereas in the case of a diameter of 100 µm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

During the data acquisition, the x-, y-, and z-coil pairs 12, 14, 16 generate a position- and time-dependent magnetic field, the applied field. This is achieved by directing suitable currents through the coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time-dependent voltage $V_k$ across the terminals of receive coil pair along the $x_k$-axis. The associated receiver converts this voltage to a signal $S_k$, which it processes further.

Figure 3:
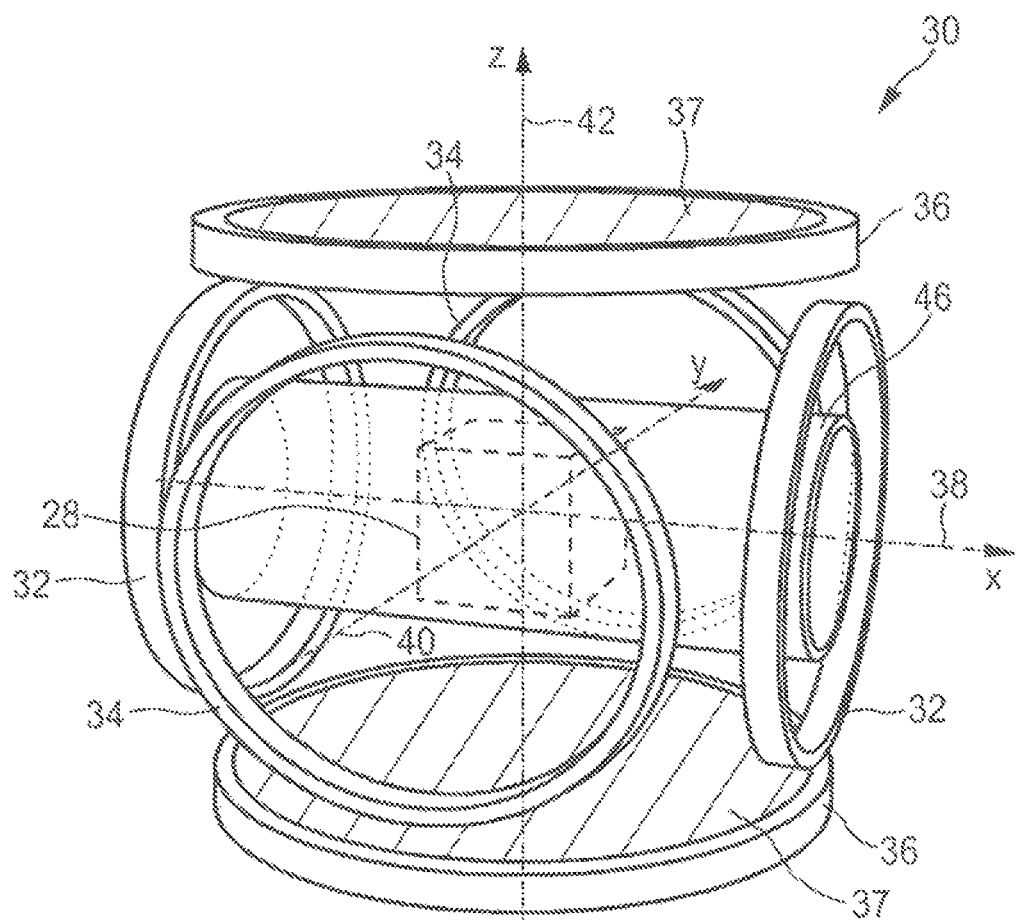
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils.

To give a few typical parameters of such an embodiment: The z-gradient of the selection field, G, has a strength of $G/\mu_0 = 2.5$ T/m, where $\mu_0$ is the vacuum permeability. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube 28 that fits into the bore 46 has an edge length of 120 mm/$\sqrt{2} \approx 84$ mm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the field of view, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

In the following, details of the present invention will be explained.

Figure 4A:
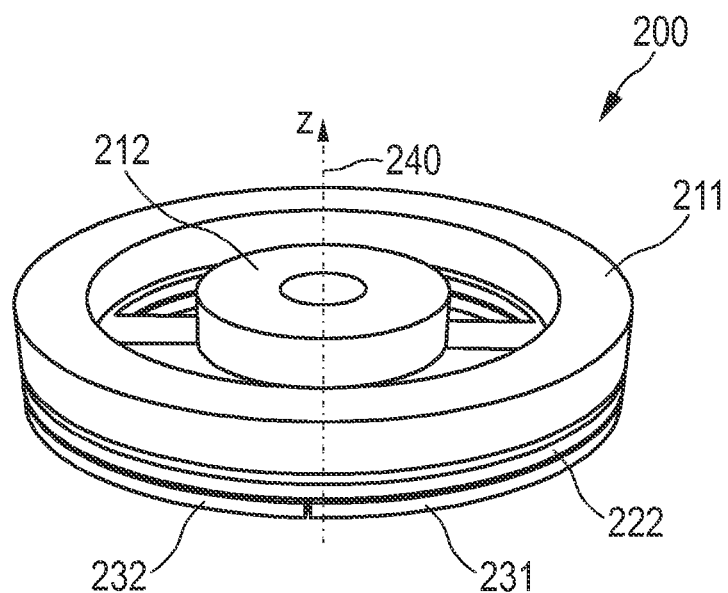
FIG. 4 shows a perspective view and a bottom view of a first embodiment of a transmit coil set as used in the device according to the present invention.
Figure 4B:
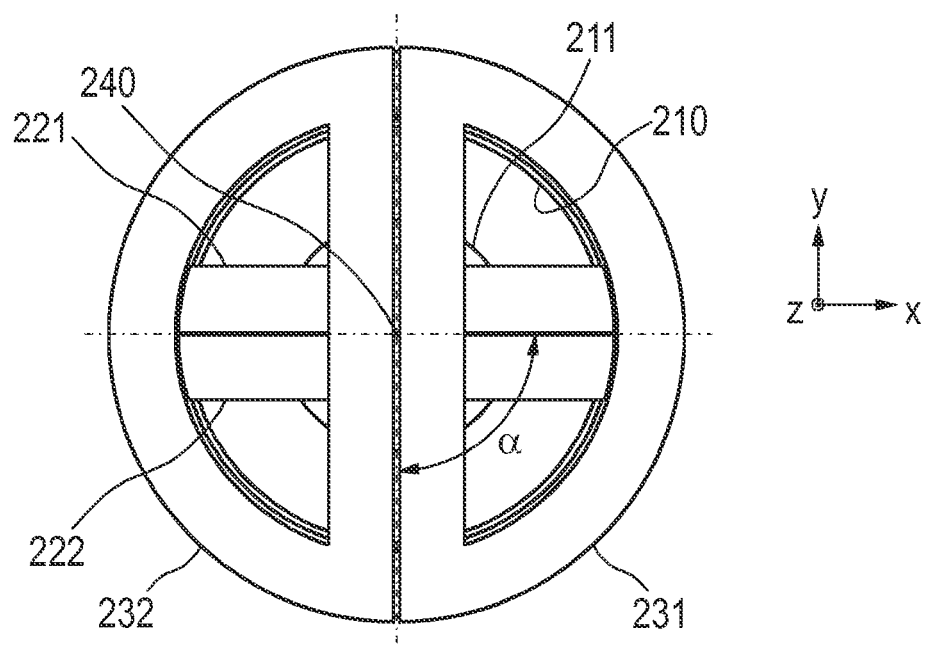
Figure 5A:
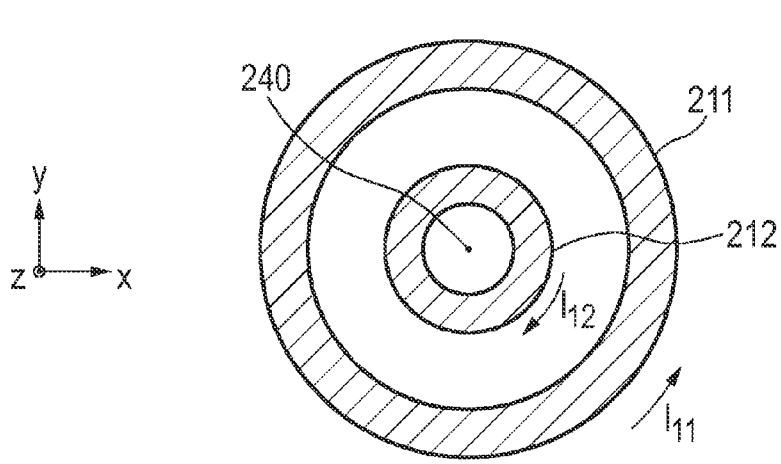
FIG. 5 shows top views on the various coils of such a transmit coil set.
Figure 5B:
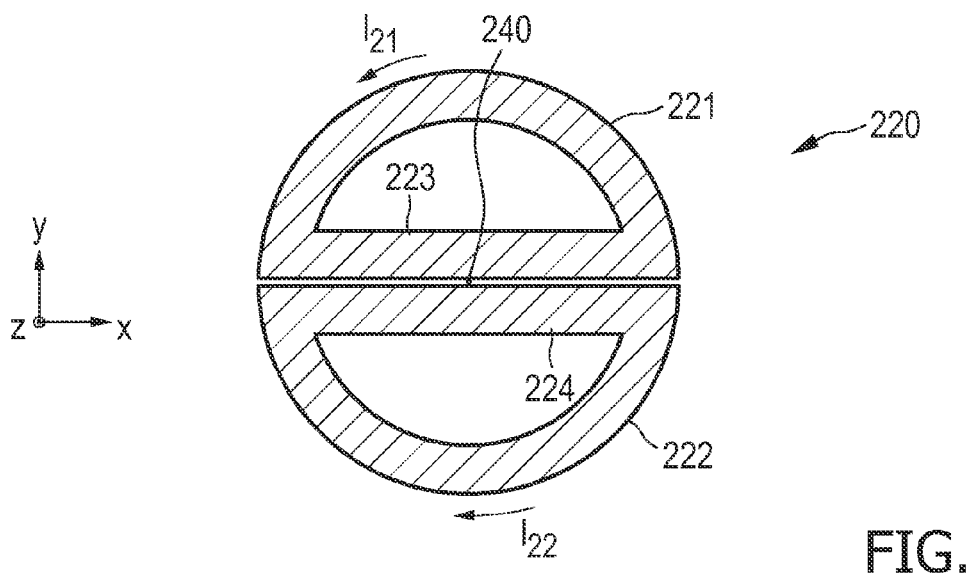
Figure 5C:
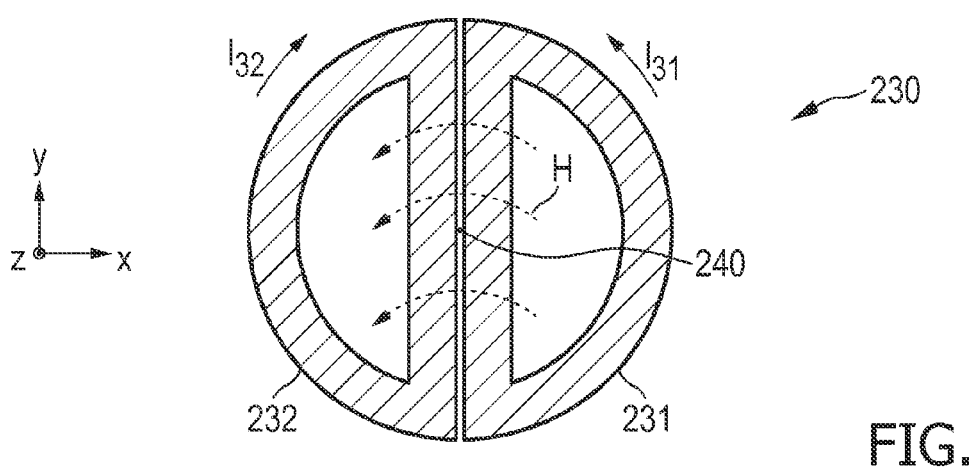

An embodiment of a single-sided transmit coil set 200 as proposed according to the present invention is shown in FIGS. 4 and 5. FIG. 4A shows a perspective view and FIG. 4B shows a side of the complete transmit coil set 200. FIGS. 5A to 5C show the various coils of the transmit coil set 200 separately as see from the top.

In this embodiment the transmit coil set 200 comprises a pair 210 of concentrically arranged selection field coils 211, 212, as shown in FIG. 5A, having the shape of rings arranged around a common coil axis 240 (arranged in z-direction) for generating the magnetic selection field. Said selection field coils 211, 212 are provided with DC currents $I_{11}, I_{12}$ of opposite direction to generate the desired gradient field as magnetic selection field having a (substantially) field-free point in the field of view.

Further, the transmit coil set 200 comprises two pairs 220, 230 of drive field coils 221, 222 and 231, 232, as separately shown in FIGS. 5B and 5C, for generating the magnetic drive fields. Said pairs 220, 230 of drive field coils 221, 222 and 231, 232 are arranged parallel to each other and to said pair 210 of selection field coils 211, 212 and are rotated with respect to each other by a rotation angle α, which may generally be in the range between 0° and 180° and which is preferably, as in this embodiment, 90°.

As shown in FIGS. 5B and 5C, each of said pairs 220, 230 of drive field coils 221, 222 and 231, 232 is formed by two neighboring coil loops, which—in this embodiment—have the form of two D-shaped coils, wherein one branch of each coil loop of a pair, e.g. the branch 223 of coil 221 and the branch 224 of coil 222, are directly arranged next to each other.

For generation of the magnetic drive fields, in particular in perpendicular directions and in a direction perpendicular to the coil axis (=z-axis), i.e. in x- and y-direction, AC currents $I_{21}$, $I_{22}$ and $I_{31}$, $I_{32}$ of respectively opposite directions are provided to the two drive field coils 221, 222 and 231, 232 of said pairs 220, 230 of drive field coils. This has the effect that the magnetic fields generated in the two drive field coils of a pair sum up together, as for instance shown in FIG. 5C partly showing the magnetic field H generated by driving currents $I_{31}$, $I_{32}$ through the two drive field coils 231, 232.

Figure 6:
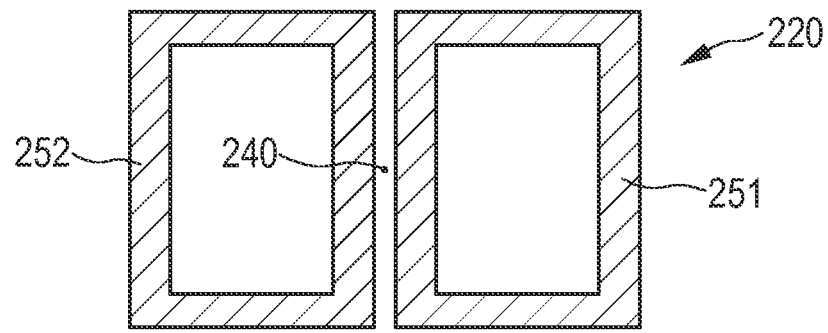
FIG. 6 shows another embodiment of a pair of drive coils according to the present invention.

An alternative shape for the drive field coils is shown in FIG. 6, showing two rectangular shaped drive field coils 251, 252 of a pair 250. Of course, other shapes of drive field coils are also possible as long as the desired magnetic drive fields can be generated for moving the FFP through the field of view.

As shown in the embodiments depicted in FIGS. 4 to 6, the two pairs 220, 230 (250) of drive field coils are preferably formed by identical coil loops. Generally, however, different coil loops can be also be used, which, however, makes it more difficult to calculate the generated magnetic field and to appropriately provide the coils with the correct drive field currents for generating the desired magnetic drive fields for moving the FFP along the desired trajectory.

Further, the two coil loops of a pair 220, 230 (250) of drive field coils are arranged symmetrical to a symmetry plane going through a coil axis 240. For instance, for the drive field coils 221, 222 shown in FIG. 5B the symmetry plane is the plane spanned by the x- and z-axis. Further, the pair 210 of selection field coils 211, 212 and the two pairs 220, 230 of drive field coils 221, 222 and 231, 232 of a transmit coil set 200 have substantially identical outer dimensions and are disk-like arranged above each other as particularly shown in FIGS. 4A and 4B leading to a compact and space-saving arrangement.

According to the present invention not a single transmit coil set 200 is provided in the MPI apparatus, but at least two, preferably a plurality of transmit coil sets 200 are provided, wherein neighboring transmit coil sets are partly overlapping each other. Such an array 300 of a plurality of communicating transmit coil sets 200 (which are only schematically indicated) is exemplarily shown as a top view in FIG. 7. The distance between the transmit coil sets 200, i.e. the actual coil overlap, depends on the particular design of the transmit coil set 200.

Figure 8A:
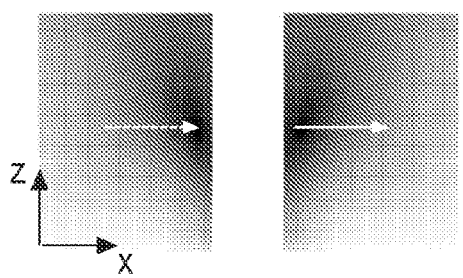
FIG. 8 illustrates the handover of the FFP between two neighboring overlapping transmit coil sets according to the present invention.
Figure 8B:
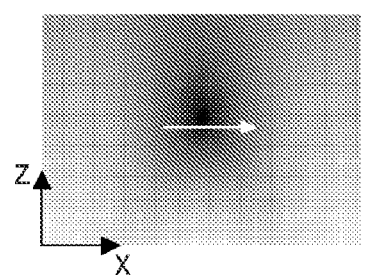
Figure 8C:
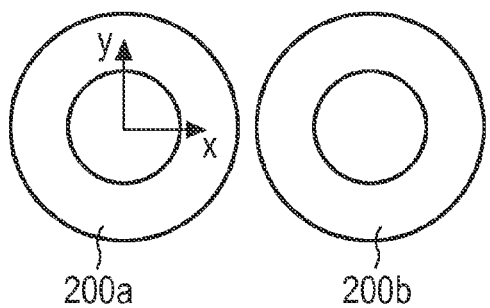
Figure 8D:
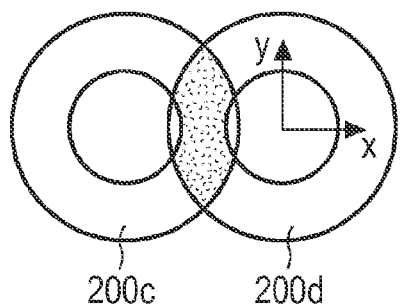

The field of view (FOV) for one transmit coil set 200 alone is relatively small. However, linear superposition of magnetic fields can be utilized to enlarge the operating range of the field-free point (FFP). FIG. 8A shows two separated FOVs generated by two separate (i.e. not overlapping) transmit coil sets 200a, 200b shown in FIG. 8C. According to the present invention, however, two neighboring transmit coil sets 200c, 200d are overlapping as shown in FIG. 8D, i.e. the distance between the two neighboring transmit coil sets 200c, 200d is decreased compared to the arrangement shown in FIG. 8C. In this way, as shown in FIG. 8B, the FFP at the right boundary of the left-hand side FOV can be fused with the FFP at the left boundary of the right-hand side FOV. In other words, in this way the transmit coil sets 200c, 200d are coupled such that communication between them is possible so that the field-free point can be operated continuously in x-direction.

Figure 7:
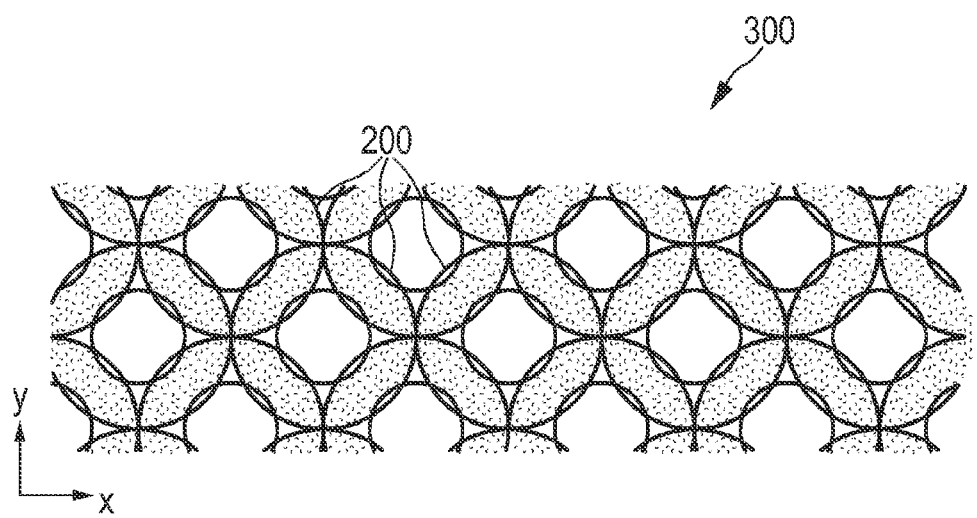
FIG. 7 shows a array of a plurality of overlapping transmit coil sets as used in an MPI apparatus according to the present invention.

The coupling between the neighboring transmit coil sets is further realized as follows. While the first transmit coil set 200c drives its FFP to the boundary of the corresponding FOV (by use of an appropriate magnetic drive field generated by its drive field coils), the magnetic gradient field (magnetic selection field) of the neighboring transmit coil set 200d is being increased preparing for the handshaking, i.e. taking over the FFP to the next domain. At the same time, the first transmit coil set 200c is decreasing its magnetic gradient field to take leave of the FFP. In this way, the field-free point can be seamlessly communicated in x- and y-direction across a field 300 of coupled transmit coil sets 200 as shown in FIG. 7. In a certain distance, e.g. if the FFPs of each second or third transmit coil set are used, this principle may operate in a parallelized way, such that multiple field-free points (mFFP) work simultaneously.

Generally, for each transmit coil set a separate receiver coil (or receiver coil set) is provided to avoid that the distance to the particles in the FFP does not become too large. In practice, only the directly adjacent receiving coils detect signals resulting from a change of the magnetic field caused by the adjacent transmit coil unit. Based thereon the minimum distance for the next FFP in the above mentioned mFFP method is determined.

For image reconstruction, it is either possible to reconstruct an image from all data detected by all receiving coils or to reconstruct partial images each from only the data detected by a single receiving coil. In the first case there is no problem, if multiple receiving coils detect the signal from the same area, but differently weighted. Ideally, the weighting for one coil is '1' and for the other coils is '0'. Generally, the size of the receiving coils is selected such that their sensitivity is restricted to a sub-area of the total field of view.

The number of transmit coil sets that are arranged in an array depends on the size of the field of view of a single transmit coil set and the desired size of the total field of view of the array. An array may, for instance, comprise only a few, tens or even hundreds of transmit coil sets.

It shall be noted that movements of the FFP are not only possible in a plane parallel to the plane of the array of transmit coil sets, but also in a direction perpendicular (i.e. z-direction) or transverse to said plane as generally described in the above mentioned paper of Sattel et al.

Further, focus field coils as commonly used in known MPI apparatus are generally not necessary, but may be used for extending the range for movement of the FOV in the direction perpendicular (i.e. z-direction) or transverse to said plane of the array of transmit coils sets.

Figure 9:
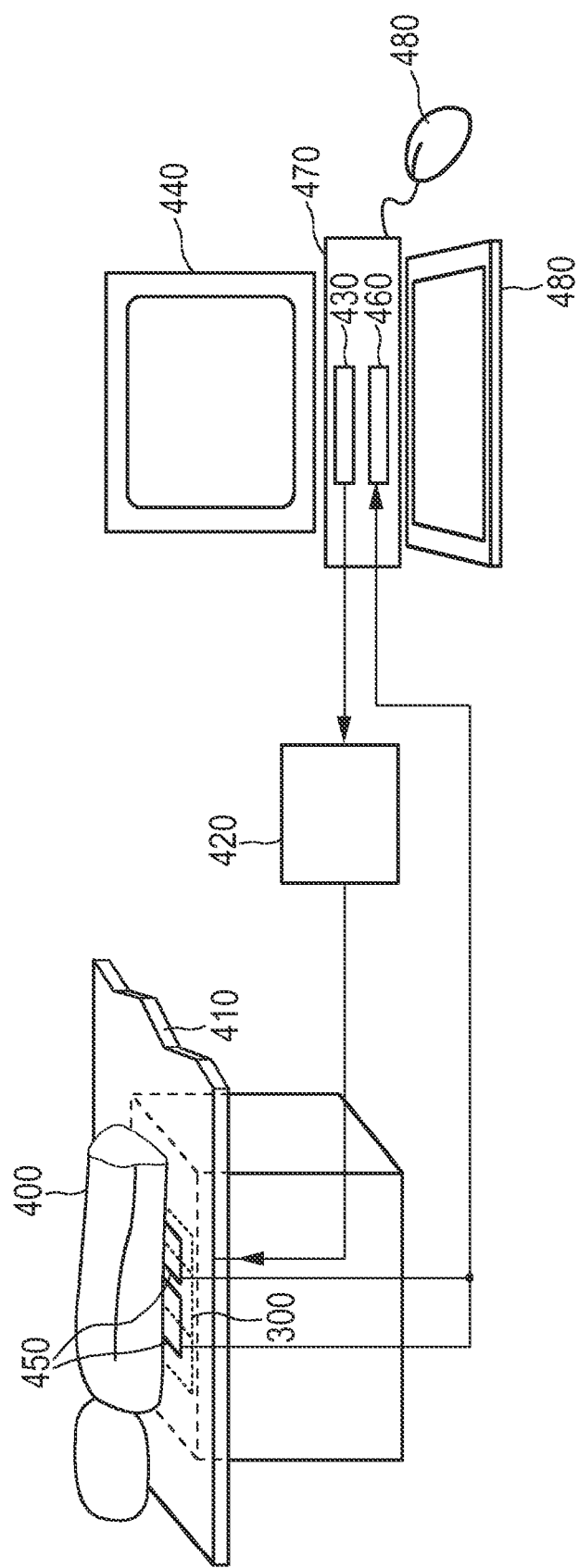
FIG. 9 shows a side view of an embodiment of an MPI apparatus according to the present invention.

A side view of an embodiment of an MPI apparatus according to the present invention is depicted in FIG. 9. A patient 400 is lying on a patient table 410, into which the array 300 of the plurality of transmit coil sets 200 is integrated. The currents for the various coils of the array 300 are generated by a generator unit 420 under control of a control unit 430. For certain applications, e.g. object movement within the patient's body (e.g. movement of a drug or a medical instrument, to which magnetic particles are adhered, to a certain position) generally no further elements are required.

For receiving detection signals for imaging purposes, which images can be displayed on a display 440, the coils of the transmit coil sets 200 used for signal transmission may be used. Another possibility is, however, to add additional receiving coils 450 with optimized properties as shown in FIG. 9. Here, sets of flat receiving coils 450 are appropriate because they can be mounted directly at the scanner front (or just below or even on top of the patient table's surface) which hardly changes the requirements on the transmit coil sets 200, while providing a higher receive sensitivity in the region of interest.

The detection signals received by the receiving coils 450 are provided to a processing unit 460, which may be part of the same workstation or computer 470 as the control unit 430. Therein, from the detection signals an image of the scanned region of the patient 400 may be reconstructed and/or said magnetic particles may be localized within the patient 400.

Figure 10:
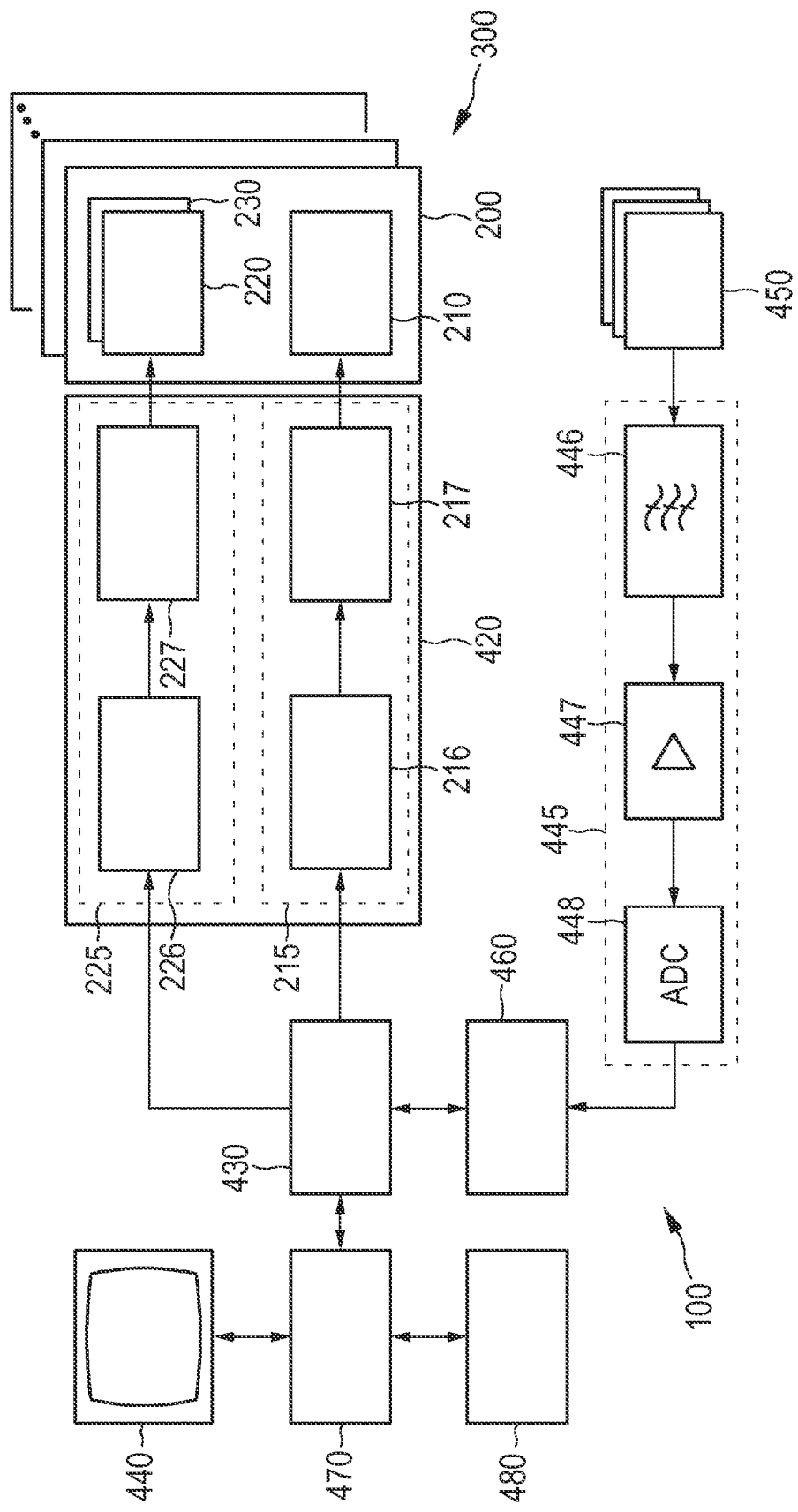
FIG. 10 shows a block diagram of an MPI apparatus according to the present invention.

FIG. 10 shows a general block diagram of an MPI apparatus 100 according to the present invention. The general principles of magnetic particle imaging explained above are valid and applicable to this embodiment as well, unless otherwise specified.

The embodiment of the apparatus 100 shown in FIG. 10 comprises an array 300 of a plurality of transmit coil sets 200 set of various coils for generating the desired magnetic fields. For generating the magnetic (gradient) selection field explained above, selection means are provided comprising at least one pair 210 of selection field (SF) coils in each transmit coil set 200. The selection means further comprises a selection field signal generator unit 215. Preferably, a separate generator subunit is provided for each coil (or each pair of coils) of the sets 210 of selection field coils. Said selection field signal generator unit 215 comprises a controllable selection field current source 216 (generally including an amplifier) and a filter unit 217 which provide the respective section field coil element with the selection field current to individually set the gradient strength of the selection field in the desired direction. Preferably, DC currents of opposite directions are provided to the coils of a pair as explained above.

The selection field signal generator unit 215 is controlled by the control unit 430, which preferably controls the selection field current generation 215 such that the sum of the field strength and the sum of the gradient strength of all spatial fractions of the selection field is maintained at a predefined level.

For generation of the magnetic drive field the apparatus 100 further comprises drive means comprising a subset of drive field (DF) coils, preferably comprising two pairs 220, 230 of drive field coils in each transmit coil set 200. The drive field coils are controlled by a drive field signal generator unit 225, preferably comprising a separate drive field signal generation subunit for each coil (or at least each pair of coils) of said set of drive field coils. Said drive field signal generator unit 225 comprises a drive field current source 226 (preferably including a current amplifier) and a filter unit 227 for providing a drive field current to the respective drive field coil. The drive field current source 226 is adapted for generating AC currents and is also controlled by the control unit 430.

For signal detection receiving means, in particular at least one receiving coil 440, and a signal receiving unit 445, which receives signals detected by said receiving means, are provided. Said signal receiving unit 445 comprises a filter unit 446 for filtering the received detection signals. The aim of this filtering is to separate measured values, which are caused by the magnetization in the examination area which is influenced by the change in position of the two part-regions (52, 54), from other, interfering signals. To this end, the filter unit 446 may be designed for example such that signals which have temporal frequencies that are smaller than the temporal frequencies with which the receiving coil 440 is operated, or smaller than twice these temporal frequencies, do not pass the filter unit 446. The signals are then transmitted via an amplifier unit 447 to an analog/digital converter 448 (ADC).

The digitalized signals produced by the analog/digital converter 448 are fed to an image processing unit (also called reconstruction means) 460, which reconstructs the spatial distribution of the magnetic particles from these signals and the respective position which the first part-region (FFP) 52 of the first magnetic field in the examination area assumed during receipt of the respective signal and which the image processing unit 460 obtains from the control unit 430.

The reconstructed spatial distribution of the magnetic particles is finally transmitted via the control unit 430 to a computer 470, which displays it on a monitor 440. Thus, an image can be displayed showing the distribution of magnetic particles in the field of view of the examination area.

Further, an input unit 480 may be provided, for example a keyboard and/or a computer mouse. A user is therefore able to set the desired direction of the highest resolution and in turn receives the respective image of the region of action on the monitor 440. If the critical direction, in which the highest resolution is needed, deviates from the direction set first by the user, the user can still vary the direction manually in order to produce a further image with an improved imaging resolution. This resolution improvement process can also be operated automatically by the control unit 430 and the computer 470. The control unit 430 in this embodiment sets the gradient field in a first direction which is automatically estimated or set as start value by the user. The direction of the gradient field is then varied stepwise until the resolution of the thereby received images, which are compared by the computer 470, is maximal, respectively not improved anymore. The most critical direction can therefore be found respectively adapted automatically in order to receive the highest possible resolution.

Figure 11:
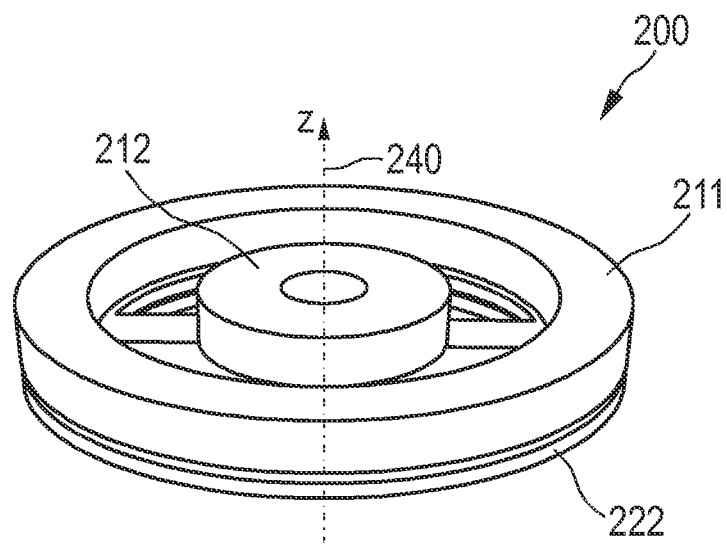
FIG. 11 shows a perspective view of a transmit coil set as used in the device according to the present invention.

With the above described embodiments of transmit coil sets 200 having two pairs 220, 230 of drive field coils and using the pair 210 of selection field coils also as a third pair of drive field coils the FFP can be moved in three dimensions so that three-dimensional imaging of an object can be performed. A perspective view of a second embodiment of a transmit coil set 200 as used in the device according to the present invention is shown in FIG. 11. In this embodiment only a single pair 220 of drive field coils 221, 222 is provided, i.e. the second pair 230 is removed from the embodiment of the transmit coil set 200 shown in FIGS. 4 and 5. This enables movement of the FFP along a line perpendicular to the coil axis 240. If additionally the pair 210 of selection field coils also as a second pair of drive field coils the FFP can be moved in two dimensions (in a plane through the coil axis) so that two-dimensional imaging of an object can be performed, e.g. to obtain a slice image. If the object is moved, e.g. by use of a moving patient table, through said plane three-dimensional imaging of the object can also be performed with such an embodiment of the transmit coil set.

The overlap of neighboring transmit coil sets generally depends on the relationship of the lateral diameter of the field of views of the individual transmit coil sets and the diameter of the outer coil of the transmit coil set. Further, the overlap depends on the size of the field of the transmit coil sets.

The size of the transmit coil set depends on the penetration depth in z-direction, the achievable currents/field strengths and the size of the field of view of the individual transmit coil sets.

The proposed arrangement allows for multi-dimensional, mFFP-imaging in an arbitrarily large field of view. Depending on the number of transmit coil sets used for this new principle, a tailored work place for catheter interventions can be realized. As mentioned above the array of transmit coils sets can be integrated into a patient table, but other arrangements are possible as well. In particular regarding the number, form and arrangement of the various coils many variations are possible, mainly dependent on the desired application of the present invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An apparatus for influencing and/or detecting magnetic particles in a field of view, which apparatus comprises:
    i) two or more transmit coil sets, wherein neighboring transmit coil sets are partially overlapping, each transmit coil set comprising:
        a pair of coplanar, concentrically arranged selection field coils for generating a magnetic selection field having a pattern in space of its magnetic field strength such that a first sub-zone having a low magnetic field strength and a second sub-zone having a higher magnetic field strength are formed in the field of view, and
        at least one pair of drive field coils for changing the position in space of the two sub-zones in the field of view by means of a magnetic drive field so that the magnetization of the magnetic particles changes locally, said at least one pair of drive field coils being arranged parallel to said pair of selection field coils and being formed by two neighboring coil loops having adjacent segments, the adjacent segments being angularly offset from adjacent segments of a neighboring pair of drive field coils,
    ii) generator means for generating current signals for provision to said selection field coils and said drive field coils for generating desired magnetic fields by said coils, and
    iii) control means for controlling said generator means to generate direct currents of opposite directions for provision to the two selection field coils of said pair of selection field coils and alternate currents of opposite directions for provision to the two drive field coils of said at least one pair of drive field coils
    wherein the control means is configured to control said generator means to generate currents for provision to the coils of the transmit coil sets such that for transfer of the first sub-zone from a first transmit coil set to a second transmit coil set the first sub-zone is driven to the border of the field of view of the first transmit coil set, the magnetic selection field of the first transmit coil set is decreased and the magnetic selection field of the second transmit coil set is increased.

2. An apparatus as claimed in claim 1,
    wherein the adjacent segments are angularly offset from adjacent segments of the neighboring pair of drive field coils by a rotation angle (α) greater than 0° and less than 180°.

3. An apparatus as claimed in claim 2,
    wherein the adjacent segments are angularly offset from the adjacent segments of the neighboring pair of drive field coils by a rotation angle (α) in the range between 75° and 105°.

4. An apparatus as claimed in claim 2,
    wherein said control means is adapted for controlling said generator means to generate alternate currents of opposite directions for provision to the two selection field coils of said pair of selection field coils in addition to the direct currents of opposite directions.

5. An apparatus as claimed in claim 1,
    wherein the at least one pair of drive field coils is formed by identical coil loops.

6. An apparatus as claimed in claim 1,
    wherein a pair of drive field coils is formed by two identical neighboring D-shaped or rectangular-shaped coil loops, wherein two linear branches of said loops are directly neighboring each other.

7. An apparatus as claimed in claim 1,
    wherein the two coil loops of a pair of drive field coils are arranged symmetrical to a symmetry plane going through a coil axis to which said selection field coils are arranged concentric.

8. An apparatus as claimed in claim 1,
    wherein the pair of selection field coils and the at least one pair of drive field coils of a transmit coil set have substantially identical outer dimensions and are disk-like arranged above each other.

9. An apparatus as claimed in claim 1, further comprising
    iv) receiving means comprising at least one receiving coil for acquiring detection signals, which detection signals depend on the magnetization in the field of view, which magnetization is influenced by the change in the position in space of the first and second sub-zone, and
    v) processing means for processing said detection signals, in particular for reconstructing an image from said detection signals and/or for localizing said magnetic particles within the field of view, in particular within an object placed within the field of view.

10. An apparatus as claimed in claim 1,
    comprising a plurality of transmit coil sets, which are equidistantly spaced and substantially arranged within one or more flat or curved planes.

11. An apparatus as claimed in claim 1, wherein the transfer of the first sub-zone from a first transmit coil set to a second transmit coil allows a field-free point having a magnetic gradient field of zero to be operated continuously between partially overlapping transmit coil sets.

12. An apparatus as claimed in claim 1,
    wherein the control means is adapted for controlling said generator means to generate currents for provision to the coils of the transmit coil sets such that two or more first sub-zones are generated and simultaneously moved.

13. A method for influencing and/or detecting magnetic particles in a field of view, which method comprises the steps of:
    i) generating magnetic fields by two or more transmit coil sets, wherein neighboring transmit coil sets are partially overlapping, said step of generating magnetic fields comprising:

generating a magnetic selection field having a pattern in space of its magnetic field strength such that a first sub-zone having a low magnetic field strength and a second sub-zone having a higher magnetic field strength are formed in the field of view by a pair of coplanar, concentrically arranged selection field coils and changing the position in space of the two sub-zones in the field of view by means of a magnetic drive field so that the magnetization of the magnetic particles changes locally by at least one pair of drive field coils, said at least one pair of drive field coils being arranged parallel to said pair of selection field coils and being formed by two neighboring coil loops having adjacent segments, the adjacent segments being angularly offset from adjacent segments of a neighboring pair of drive field coils, ii) generating, with a generator means, current signals for provision to said selection field coils and said drive field coils for generating desired magnetic fields by said coils, and iii) controlling, with a control means, said generator means to generate direct currents of opposite directions for provision to the two selection field coils of said pair of selection field coils and alternate currents of opposite directions for provision to the two drive field coils of said at least one pair of drive field coils wherein the control means is configured to control said generator means to generate currents for provision to the coils of the transmit coil sets such that for transfer of the first sub-zone from a first transmit coil set to a second transmit coil set the first sub-zone is driven to the border of the field of view of the first transmit coil set, the magnetic selection field of the first transmit coil set is decreased and the magnetic selection field of the second transmit coil set is increased.

14. A non-transitory computer readable storage medium comprising a computer readable program for influencing and/or detecting magnetic particles in a field of view, wherein the computer readable program when executed on a computer causes the computer to perform the steps of claim 13, wherein the computer is the control means.

* * * * *